(12) United States Patent
Stevenson et al.

(10) Patent No.: US 8,278,490 B2
(45) Date of Patent: Oct. 2, 2012

(54) PHASE TRANSFER CATALYST FOR SYNTHESIS OF PENTAERYTHRITOL DIPHOSPHITES

(75) Inventors: Donald Stevenson, Dover, OH (US); Ping Lue, Garnet Valley, PA (US); Jacob M. Lance, Dover, OH (US)

(73) Assignee: Dover Chemical Corporation, Dover, OH (US)

( * ) Notice: Subject to any disclaimer, the term of this patent is extended or adjusted under 35 U.S.C. 154(b) by 185 days.

(21) Appl. No.: 12/838,694

(22) Filed: Jul. 19, 2010

(65) Prior Publication Data

US 2011/0021839 A1    Jan. 27, 2011

Related U.S. Application Data

(60) Provisional application No. 61/228,334, filed on Jul. 24, 2004.

(51) Int. Cl.
*C07C 9/576* (2006.01)

(52) U.S. Cl. ......................................................... 568/12
(58) Field of Classification Search ..................... 568/12
See application file for complete search history.

(56) References Cited

U.S. PATENT DOCUMENTS

| | | | |
|---|---|---|---|
| 3,310,609 A | 3/1967 | Baranauckas et al. | |
| 4,305,866 A | 12/1981 | York et al. | |
| 4,665,211 A | 5/1987 | Marlin et al. | |
| 4,739,090 A * | 4/1988 | Tajima et al. | 558/78 |
| 5,103,035 A | 4/1992 | Elnagar et al. | |
| 5,364,895 A | 11/1994 | Stevenson et al. | |
| 5,438,086 A | 8/1995 | Stevenson et al. | |
| 7,342,060 B2 | 3/2008 | Larke | |

\* cited by examiner

*Primary Examiner* — Sikarl Witherspoon
(74) *Attorney, Agent, or Firm* — Hahn Loeser & Parks LLP

(57) ABSTRACT

The present invention pertains to a process for the preparation of pentaerythritol diphosphites via a one-pot, direct esterification of phosphorus trichloride with pentaerithritol, and either an alkylphenol or an arylalkylphenol which functions both as a reactant and as a solvent, with a phase transfer catalyst such as a quaternary ammonium salt.

11 Claims, No Drawings

US 8,278,490 B2

PHASE TRANSFER CATALYST FOR SYNTHESIS OF PENTAERYTHRITOL DIPHOSPHITES

CROSS-REFERENCE TO RELATED APPLICATIONS/INCORPORATION BY REFERENCE

This patent application claims priority to and the benefit of U.S. Provisional Patent Application Ser. No. 61/228,334 which was filed on Jul. 24, 2009, and is incorporated herein by reference in its entirety.

TECHNICAL FIELD

The present invention pertains to a process for preparing pentaerythritol diphosphites which are useful as stabilizers for polymer compositions. More specifically, the present invention is directed to a process for the preparation of pentaerythritol diphosphites via a one-pot, direct esterification of phosphorus trichloride with pentaerithritol, and an alkylphenol or an arylalkylphenol which itself functions as both a solvent and a reactant, with a phase transfer catalyst.

BACKGROUND OF THE INVENTION

At least one purpose associated with the addition of a stabilizer to a polymeric resin is to prevent deterioration of the polymers derived from the resin during processing at high temperatures and also to permit the manufacture of products with increased intrinsic quality attributable at least in part to increased resistance to thermal and light degradation during their intended use.

Many organic phosphites have been used as stabilizers. Among them are the commercially significant pentaerythritol diphosphites with either a spiro configuration or a caged configuration. These pentaerythritol diphosphites are particularly useful since they are thermally stable, have a high decomposition temperature and are of low volatility. Their high degree of intrinsic stability, especially under conditions of high humidity, is at least partially responsible for their satisfactory performance in inhibiting discoloration of polyolefins, typically caused by high temperature.

Many processes have been proposed for producing bis (alkylphenyl)pentaerythritol phosphites. Phosphites of this type have generally in the past been prepared by one of two methods: (a) the reaction of an alkylphenol with dichloropentaerythritol disphosphide, as shown in U.S. Pat. No. 3,310,609, and (b) sequential transesterification reactions beginning with the reaction of pentaerythritol with an appropriate trialkylphosphite or triphenylphosphite to form pentaerythritol diphosphite which then undergoes the second transesterification reaction with an alcohol or a phenol, to form the desired bis(alkyl) or bis(alkylphenyl)pentaerythritol diphosphite, as illustrated in U.S. Pat. Nos. 4,305,866 and 4,665,211.

Although the aforementioned methods are useful they each suffer from certain disadvantages. The first identified method requires the use of a solvent because of the solid nature of pentaerythritol. The use of a solvent represents an additional cost and it must be removed and recovered, all of which negatively impact the process economics and steps required to synthesize a final product. The second method also has its own disadvantages such as multiple steps, each of which requires purification, which tends to add long reaction cycles, low yield and additional expense.

U.S. Pat. No. 5,103,035 also teaches a method for preparing pentaerythritol diphosphites in a chlorinated solvent and in the presence of a heterocyclic tertiary amine catalyst. Although it is stated that a highly pure product was obtained, the process involves multiple steps, e.g., adding ammonia gas to remove residual hydrogen chloride or other bound acid species, followed by filtering to remove ammonium salts, and crystallizing the product with isopropyl alcohol. These additional steps result in a relatively low yield.

U.S. Pat. No. 5,364,895 also teaches a method for preparing pentaerythritol diphosphites which involves a solvent such as heptane and/or toluene and the reactants 2,4-dicumylphenol and $PCl_3$ and pentaerythritol, optionally with the addition of a trialkanol amine.

U.S. Pat. No. 5,438,086 also teaches a method for preparing pentaerythritol diphosphites which involves a transesterification reaction of triphenylphosphite with pentaerythritol and phenol using a sodium metal catalyst; followed by distillation to remove unwanted by-products followed by the addition of dicumylphenol and a sodium metal catalyst.

Thus, it is apparent that method for effective preparation of bis(alkylphenyl)pentaerythritol diphosphites in a more economical way while achieving high yield and high purity is still to be sought.

SUMMARY OF THE INVENTION

The process of the present invention involves in-situ formation of a bis(alkylphenyl)pentaerythritol diphosphite of high spiro content, preferably greater than 90%, more preferably greater than or equal to 93%, by adding phosphorus trichloride to a reaction vessel previously charged with pentaerythritol, an alkylphenol or an arylalkylphenol and a phase transfer catalyst. The alkylphenol in this case is not only a reactant but also a solvent.

The invention encompasses a process for the in-situ formation of a bis(alkylphenyl)pentaerythritol diphosphite

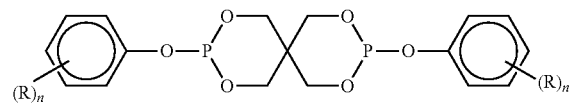

wherein R is independently selected from the group consisting of $C_{1-22}$ alkyls, $C_{2-22}$ alkoxy, $C_{3-22}$ alkenyls, $C_{6-40}$ phenyl, $C_{7-40}$ alkylaryls and $C_{7-40}$ arylalkyls, and n is an integral value ranging from 2 to 4 inclusive, comprising the steps of: adding phosphorus trichloride ($PCl_3$) to a reaction vessel previously charged with pentaerythritol

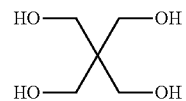

adding a phenol selected from the group consisting of alkylphenol and arylalkylphenol

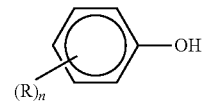

wherein R and n are as defined previously, the phenol acting as both a reactant and a solvent for the reaction; and adding a phase transfer catalyst.

The phase transfer catalyst is selected from the group consisting of a quaternary ammonium salt or a quaternary phosphonium salt selected from the group consisting of

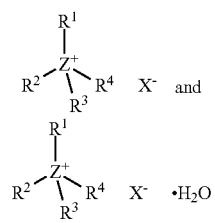

wherein $R^1$-$R^4$ are independently selected from the group consisting of $C_{1-20}$ alkyl groups, $C_{2-24}$ alkoxy, $C_{3-24}$ alkenyls, $C_{6-45}$ phenyl including fused aromatic rings, $C_{7-45}$ alkylaryls and $C_{7-45}$ arylalkyls, Z is selected from the atoms consisting of N and P, and further wherein X is selected from the group consisting of halides (fluoride, chloride, bromide, iodide), sulfates, bisulfates, hydroxyl and further wherein any of $R^1$-$R^4$ may be covalently bonded to each other.

These and other objects of the present invention will become more readily apparent from a reading of the following detailed description, and with further reference to the appended claims.

DETAILED DESCRIPTION OF THE INVENTION

As used herein, the following terms have the identified meanings: (a) "alkyl" refers to a straight or branched chain monovalent hydrocarbon radical; (b) "alkenyl" refers to a straight or branched chain monovalent hydrocarbon radical having at least two carbons joined by a carbon-carbon double bond; (c) "aryl" refers to a monovalent aromatic benzene ring radical, or to an optionally substituted benzene ring system radical system fused to at least one optionally substituted benzene rings; (c) "cycloalkyl" refers to a non-aromatic alicyclic monovalent hydrocarbon radical having at least three carbon atoms; (d) "cycloalkylene" refers to a non-aromatic alicyclic divalent hydrocarbon radical having at least three carbon atoms, with at least one degree of unsaturation; (e) "alkylaryl" refers to an alkyl group as defined above substituted onto an aryl as defined above; (f) "arylalkyl" refers to an aryl group as defined above substituted onto an alkyl as defined above; (g) "alkoxy" refers to an alkyl group as defined above connected through an oxygen radical to an adjoining group; and (h) "aryloxy" refers to an aryl group as defined above connected through an oxygen radical to an adjoining group.

The process of the present invention involves the in-situ formation of a bis(alkylphenyl)pentaerythritol diphosphite

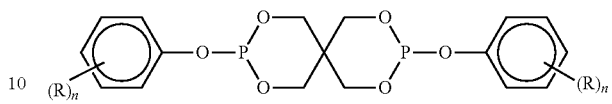

wherein R is independently selected from the group consisting of $C_{1-22}$ alkyl, $C_{1-22}$ alkoxy, $C_{3-22}$ alkenyl, $C_{6-40}$ aryl, $C_{7-40}$ cycloalkyl, $C_{7-40}$ cycloalkylene, $C_{7-40}$ alkylaryl, $C_{7-40}$ arylalkyl, $C_{7-40}$ aryloxy, and n is an integral value ranging from 2 to 4 inclusive, more preferably, a bis(2,6-di-t-butyl-4-methylphenyl)pentaerythritol diphosphite

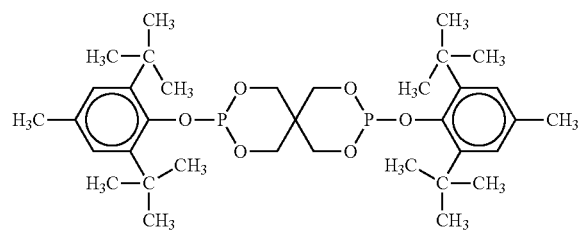

or a bis(2-t-butyl-4-nonylphenyl)pentaerythritol diphosphite

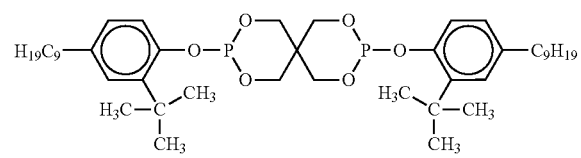

most preferably, a bis(2,4-dicumylphenyl)pentaerythritol diphosphite

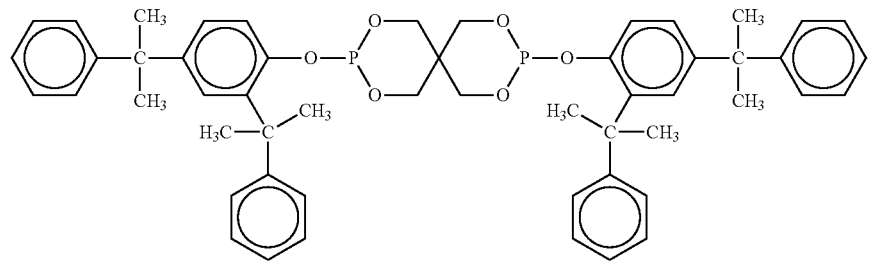

by adding phosphorus trichloride ($PCl_3$) to a reaction vessel previously charged with pentaerythritol

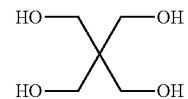

and an alkylphenol or an arylalkylphenol

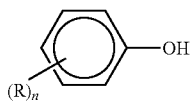

wherein R and n are as previously defined and wherein the phenol acts as both a reactant and a solvent for the reaction. In one embodiment, the alkylphenol is 2,6-di-t-butyl-4-methylphenol,

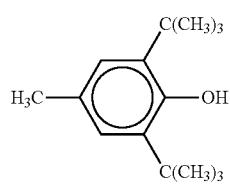

or 2-t-butyl-4-nonylphenol

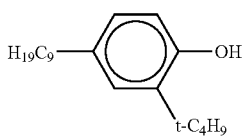

and in another embodiment, the alkylphenol is an alkylarylphenol, e.g., 2,4-dicumylphenol,

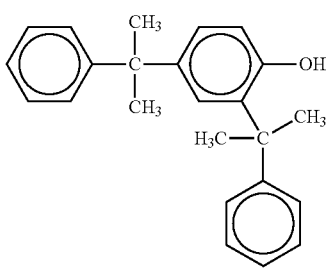

with a phase transfer catalyst, preferably a quaternary ammonium salt or a quaternary phosphonium salt, more preferably a quaternary ammonium salt.

The mole ratio of phosphorus trichloride and pentaerythritol used in forming the product is from about 1.9 to 2.2 moles of phosphorus trichloride per mole of pentaerythritol. In a preferred embodiment, the mole ratio is 2.0 to 1.0. The use of less than two moles of phosphorus trichloride per mole of pentaerythritol can result in a low yield of the product and leave excess residual pentaerythritol which may cause quality issues and require additional step(s) for removal. The use of more than two moles of phosphorus trichloride per mole of pentaerythritol can result in the formation of undesirable phosphorus by-products which may also cause product quality issues and require additional process step(s) for their removal.

The catalyst used in the reaction is a phase transfer catalyst, used in an amount which is within the range of 1.0 to 15 weight percent based on the amount of pentaerythritol charged. In a preferred embodiment, the amounts are within 3.0 to 5.0 weight percent of pentaerythritol.

Many phase transfer catalysts can be used for the reaction. The preferred catalysts are quaternary ammonium salts:

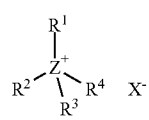

which may include water of hydration and/or crystallization

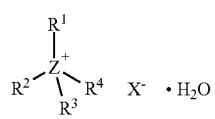

and wherein $R^1$-$R^4$ are independently selected from the group consisting of $C_{1-20}$ alkyl groups, $C_{2-24}$ alkoxy, $C_{3-24}$ alkenyls, $C_{6-45}$ phenyl including fused aromatic rings, $C_{7-45}$ alkylaryls and $C_{7-45}$ arylalkyls, Z is selected from the atoms consisting of N and P, and further wherein X is selected from the group consisting of halides (fluoride, chloride, bromide, iodide), sulfates, bisulfates, hydroxyl and further wherein any of $R^1$-$R^4$ may be covalently bonded to each other.

Exemplary but non-limiting examples would include: benzyltriethylammonium bromide or chloride, hexadecyltrimethylammonium bromide or chloride, tetrabutylammonium bromide or chloride, tetramethylammonium bromide or chloride, tetraethylammonium bromide or chloride, etc. The catalyst can also be comprised of a mixture of two or more of the foregoing. Examples of mixtures include tetramethylammonium bromide or chloride and tetrabutylammonium bromide or chloride; tetramethylammonium bromide or chloride and tetraethylammonium bromide or chloride; tetrabutylammonium bromide or chloride and tetraethylammonium bromide or chloride, etc. The preferred catalysts are benzyltriethylammonium halides and hexadecylammonium halides. The most preferred are benzyltriethylammonium halides.

The alkylphenol used in the process is preferably an alkylphenol wherein the alkyl group has aromaticity, most preferably a dialkylphenol because of the superior thermal stability of the diphosphite which results from the reaction. The most preferred are those dialkylphenols which contain alkyl groups such as tertiary butyl, cumyl, tertiary amyl, secondary butyl. The illustrated examples use 2,4-dicumylphenol although the invention is not limited to the use of this reactant.

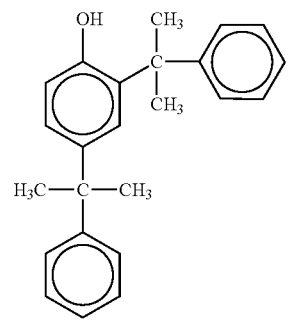

The process conditions typically involve mixing pentaerythritol and the catalyst in the dialkylphenol which is present in excess. Depending on the dispersibility of the resultant diphosphite product, the excess amount of the dialkylphenol ranges from 1 to 10 times of the stoichiometric amount of the phenol. The preferred excess amount is from 2-4 times. The mixture is kept at a temperature sufficient to make it free flowing and well stirred while mild enough not to cause phosphorus trichloride evaporate and condense excessively. The preferred temperature range is from 40° C. to 100° C. To ensure pentaerythritol and the catalyst dispersed sufficiently in the dialkylphenol, it is preferred to mix for at least 0.5 to 4 hours before proceeding to the next step.

Phosphorus trichloride, which is a liquid under process conditions, is added to the aforementioned mixture at a rate which is sufficient for pentaerythritol and the catalyst to interact without causing side products to form and/or an unnecessary length of reaction time. If the rate of addition is too fast side reactions can occur. Conversely, if the rate of addition is too slow in the process of the product formation the viscosity of the mixture will increase significantly so that the reminder of the phosphorus trichloride does not effectively react with the pentaerythritol and by-products will form. In addition, it will increase unnecessarily the reaction time. The preferred addition time is from 1 to 2 hours.

After phosphorus trichloride is added, the resultant reaction mixture is heated gradually to a temperature within the range of from about 120° C., to about 180° C., and preferably within the range of from 140° C., to about 145° C. The duration of heating up is from 0.5 hour to 4 hours, preferably from 1 hour to 2 hours. During the course of heating up, depending on the physical properties of the product and the solubility of the product in the dialkylphenol, the reaction mass will become increasingly viscous while the product continues to form. To ensure a high yield and a high purity of the product, the reaction mixture needs to be well mixed. It is advisable to use multi-levels of agitators and agitators designed to create a turbine effect.

To obtain good yields and a low acid value of the product, say less than 1.0 mg KOH/g gram sample, a nitrogen sparge is applied to the reaction mass while it is kept at the above described temperature. The duration of the nitrogen sparge will be within the range of from about 4 to about 16 hours, and preferably within the range of about 8 to 12 hours. Since HCl is evolved during the nitrogen sparge, monitoring of the HCl evolution for its cessation is a convenient way to decide the duration time of nitrogen sparge needed for each particularly designed process to obtain its maximum yield and possibly lowest acid value of bis(alkylphenyl)pentaerythritol diphosphite. Alternatively, a process sampling technique is used to measure the acid value and thus, the progress of the reaction, to determine the duration.

When a lower Acid Value is obtained and/or the Acid Value does not change after two consecutive in process samples measurement, the recovery of the desired bis(alkylphenyl)pentaerythritol diphosphite can be affected. A recovery sequence, which gives a very pure product, includes: (a) adding an aromatic diluent, such as xylene or toluene; (b) cooling the reaction mass to room temperature; (c) collecting the solid bis(alkylphenyl)pentaerythritol diphosphite by filtration; (d) washing the solid bis(alkylphenyl)pentaerythritol diphosphite filtration cake with the same aromatic diluent used in (a) to remove the excess alkylphenol used for the preparation. The preferred diluent is xylene. Other diluent can be used provided that the bis(alkylphenyl)pentaerythritol diphosphite product is essentially insoluble therein.

Other than the recovery method described above, the recovery of the bis(alkylphenyl)pentaerythritol diphosphite product can also be effected by simply evaporating all the excess alkylphenol which is present as a solvent. This can be achieved by distilling off the excess alkylphenol at a temperature in the range of from about 100° C., to about 300° C., and a pressure of about full vacuum to about 200 mm Hg absolute. This is a preferred method, provided the final bis(alkylphenyl)pentaerythritol diphosphite product is pure enough to maintain its efficacy as a stabilizer for polymer compositions, because a maximum yield of the product can be obtained in a most simplified operation. The recovered alkylphenol is of high purity and can be recycled back as raw material for subsequent preparation of the bis(alkylphenyl)pentaerythritol diphosphite. In one preferred embodiment, the alkylphenol is 2,4-dicumylphenol and the bis(alkylphenyl)pentaerythritol diphosphite is bis(2,4-dicumylphenyl) pentaerythritol diphosphite.

EXAMPLES

The best mode for carrying out the invention will now be described for the purpose of illustrating the best mode known to the applicants at the time. The examples are illustrative only and not meant to limit the invention, as measured by the scope and spirit of the claims.

Example #1

To a 500 mL flask equipped with a mechanical stirrer, a condenser, and a caustic scrubber was added molten 2,4-dicumylphenol (265 g) and benzyltriethylammonium bromide (BTEAB, 2 g). The mixture was mixed well and heated to 79-81° C. To this mixture was added pentaerythritol (PE, 13.3 g, 97.7 mmols). The solution was mixed thoroughly for 2 hours to ensure a good dispersion of the PE and the catalyst. $PCl_3$ (27.7 g, 201.7 mmols) was added over about a 1 hour period. Hydrogen chloride (HCl) gas started to evolve while $PCl_3$ was added. Evolved HCl was trapped in the caustic scrubber. After 1 hour of heating the reaction mixture became thick and white solids started to appear. A nitrogen sparge was then applied and the reaction temperature was slowly raised to 140-142° C. A sample was taken and was analyzed to have an Acid Value of 0.9. The mixture was nitrogen sparged continuously for about 12 hours and the Acid Value was 0.3. 250 g of xylene were added and the reaction was cooled to room temperature. The product was collected by filtration, washed with xylene and oven dried. The dried product weighed 76.7 grams (92% yield based on the PE charged). The product had an Acid Value of 0.02, >93% spiro and 0.42% DCP.

Example #2

The apparatus and the charges in Example #1 were used again except tetramethylammonium chloride (TMAC, 1 g) was used as the catalyst. The reaction was carried out in a same manner as Example 1. The in-process sample before nitrogen sparge was analyzed to have an Acid Value of 1.1. The mixture was nitrogen sparged continuously for about 12 hours and the Acid Value was 0.4. 250 g of xylene was added and the reaction was cooled to room temperature. The product was collected by filtration, washed with xylene and oven dried. The dried product weighed 73.3 grams (88% yield based on the PE charged). The product had an Acid Value of 0.01, 93% spiro and 0.42% DCP.

Example #3

The apparatus in Example #1 was used again except in this case, a mixture of two catalysts, tetraethylammonium bromide (TEAB 1 g), and tetramethylammonium chloride (TMAC, 1 g), was used. Molten 2,4-dicumylphenol (265 g) and the mixture of the catalysts were mixed well and heated to 79-81° C. To this mixture was added pentaerythritol (PE, 13.3 g, 97.7 mmols). The solution was mixed thoroughly for ½ hour to ensure a good dispersion of the PE and the catalysts. $PCl_3$ (27.7 g, 201.7 mmols) was added over about a 1 hour period. Hydrogen chloride (HCl) gas started to evolve while $PCl_3$ was added in. Evolved HCl was trapped in the caustic scrubber. After 1 hour of heating the reaction mixture became thick and white solids started to appear. A nitrogen sparge was then applied and the reaction temperature was slowly raised to 140-142° C. A sample was taken and was analyzed to have an Acid Value of 1.7. The mixture was nitrogen sparged continuously for about 12 hours and the Acid Value was 0.5. 250 g of xylene was then added and the reaction was cooled to room temperature. The product was collected by filtration, washed with xylene and oven dried. The dried product weighed 76.5 grams (92% yield based on the PE charged). The product was analyzed to have an Acid Value of 0.01, 93% spiro and 0.32% DCP.

Example #4

The apparatus, the charges and the procedures outlined in Example #1 were used except tetraethylammonium bromide (TEAB, 2 g) was used as the catalyst. A sample taken after nitrogen sparge continuously for 12 hours was analyzed to have an Acid Value of 0.4. The product was collected by filtration, washed with xylene and oven dried. The dried product weighed 74.8 grams (90% yield based on the PE charged). The product was analyzed to have an Acid value of 0.01, 93% spiro, and 0.22% DCP.

Example #5

The apparatus in Example #1 was used. 2,4-dicumylphenol (265 g) and hexadecyltrimethylammonium bromide (HT-MAB 2 g) were mixed well and heated to 85-86° C. To this mixture was added pentaerythritol (PE, 13.3 g, 97.7 mmols). The solution was mixed thoroughly for 1 hour to ensure a good dispersion of the PE and the catalyst. $PCl_3$ (27.7 g, 201.7 mmols) was added over about a 1 hour period. After 1 hour of heating the reaction mixture became thick and white solids started to appear. A nitrogen sparge was then applied and the reaction temperature was slowly raised to 140-142° C. A sample was taken and was analyzed to have an Acid Value of 1.1. The mixture was nitrogen sparged continuously for about 12 hours and the Acid Value was 0.2. 250 g of xylene were then added and the reaction was cooled to room temperature. The product was collected by filtration, washed with xylene and oven dried. The dried product weighed 73.4 grams (88% yield based on the PE charged). The product had an Acid Value of 0.01, 93% spiro and 0.29% DCP.

Example #6

To a 500 mL flask equipped with a mechanical stirrer, a condenser, and a caustic scrubber was added molten 2,4-dicumylphenol (DCP, 265 g) and tetrabutylammonium bromide (TBAB, 1.4 g). The mixture was mixed well and heated to 92-94° C. To this mixture was added pentaerythritol (PE, 13.3 g, 97.7 mmols). The solution was mixed thoroughly for 2 hours to ensure a good dispersion of the PE and the catalyst. $PCl_3$ (27.7 g, 201.7 mmols) was added over about a 1 hour period. Hydrogen chloride (HCl) gas started to evolve while $PCl_3$ was added in. Evolved HCl was trapped in the caustic scrubber. After 1 hour of heating the reaction mixture became thick and white solids started to appear. A nitrogen sparge was then applied and the reaction temperature was slowly raised to 140-142° C. A sample was taken and was analyzed to have an Acid Value of 0.8. The mixture was nitrogen sparged continuously for about 12 hours and the Acid Value was 0.5. The temperature was then raised to 200° C. and vacuum (0.3 mmHg) was applied to remove the excess DCP. DCP was stripped out between 200° C. and 260° C. The vacuum stripped product contained 4.8% DCP and had an Acid Value of 0.47. The vacuum stripped DCP was found to be >99% pure.

This example illustrates that excess 2,4-dicumylphenol (DCP) can be removed by vacuum distillation. The example, however, only shows the results of the apparatus and process conditions applied at the time when the invention was put into practice in a laboratory scale. In reality, a better evaporation method, such as thin film distillation, and a vacuum up to 0.01 mm Hg, can be used to remove excess 2,4-dicumylphenol to levels below 0.5%. Such process had been disclosed in U.S. Pat. No. 7,342,060 B2.

The best mode for carrying out the invention has been described for the purposes of illustrating the best mode known to the applicant at the time. The examples are illustrative only and not meant to limit the invention, as measured by the scope and spirit of the claims. The invention has been described herein with reference to the disclosed embodiments. Obviously, modifications and alterations will occur to others upon a reading and understanding of this specification. It is intended to include all such modifications and alterations insofar as they come within the scope of the appended claims or the equivalence thereof.

What is claimed is:

1. A process for the in-situ formation of a bis(alkylphenyl) pentaerythritol diphosphite

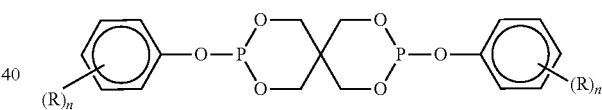

wherein R is independently selected from the group consisting of $C_{1-22}$ alkyl, $C_{1-22}$ alkoxy, $C_{3-22}$ alkenyl, $C_{6-40}$ aryl, $C_{7-40}$ cycloalkyl, $C_{7-40}$ cycloalkylene, $C_{7-40}$ alkylaryl, $C_{7-40}$ arylalkyl, $C_{7-40}$ aryloxy, and n is an integral value ranging from 2 to 4 inclusive, comprising the steps of:

adding phosphorus trichloride ($PCl_3$) to a reaction vessel previously charged with pentaerythritol

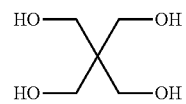

adding a phenol selected from the group consisting of alkylphenol and arylalkylphenol

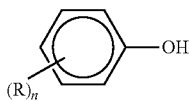

wherein R and n are as defined previously, the phenol acting as both a reactant and a solvent for the reaction; and adding a phase transfer catalyst.

2. The process of claim 1 wherein said phase transfer catalyst is selected from the group consisting of a quaternary ammonium salt and a quaternary phosphonium salt.

3. The process of claim 2 wherein said quaternary salt is selected from the group consisting of

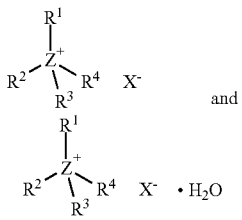

wherein $R^1$-$R^4$ are independently selected from the group consisting of $C_{1-20}$ alkyl groups, $C_{2-24}$ alkoxy, $C_{3-24}$ alkenyls, $C_{6-45}$ phenyl including fused aromatic rings, $C_{7-45}$ alkylaryls and $C_{7-45}$ arylalkyls;

Z is selected from the atoms consisting of N and P, and further wherein

X is selected from the group consisting of halides (fluoride, chloride, bromide, iodide), sulfates, bisulfates, hydroxyl and further wherein any of $R^1$-$R^4$ may be covalently bonded to each other.

4. The process of claim 3 wherein said quaternary ammonium salt is selected from the group consisting of benzyltriethylammonium halide, hexadecyltrimethylammonium halide, tetrabutylammonium halide, tetramethylammonium halide, tetraethylammonium halide and mixtures thereof.

5. The process of claim 3 wherein said halide is selected from the group consisting of chloride and bromide.

6. The process of claim 1 wherein said alkylphenol is 2,6-di-t-butyl-4-methylphenol,

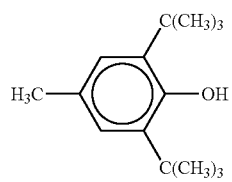

and said arylalkylphenol is 2,4-dicumylphenol

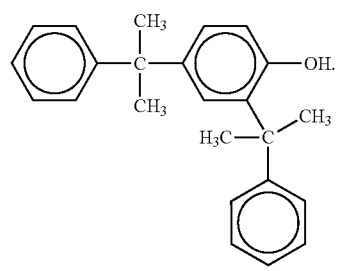

7. The process of claim 1 wherein said arylalkylphenol is 2,4-dicumylphenol

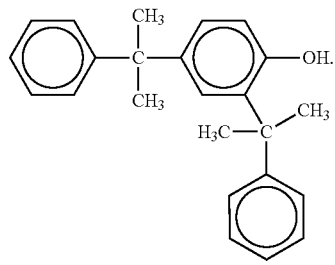

8. The process of claim 6 wherein said bis(alkylphenyl)pentaerythritol diphosphite is selected from the group consisting of bis(2,6-di-t-butyl-4-methylphenyl)pentaerythritol diphosphite

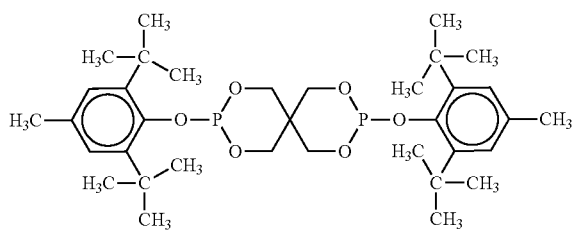

bis(2-t-butyl-4-nonylphenyl)pentaerythritol diphosphite,

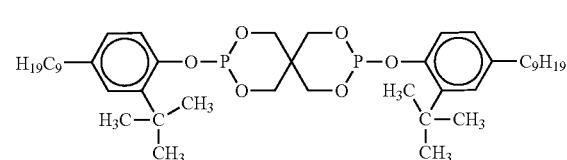

and bis(2,4-dicumylphenyl)pentaerythritol diphosphite

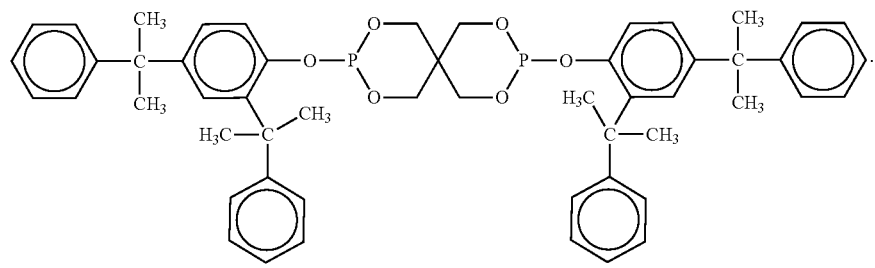

9. The process of claim 6 wherein
said bis(alkylphenyl)pentaerythritol diphosphite is bis(2,4-dicumylphenyl)pentaerythritol diphosphite

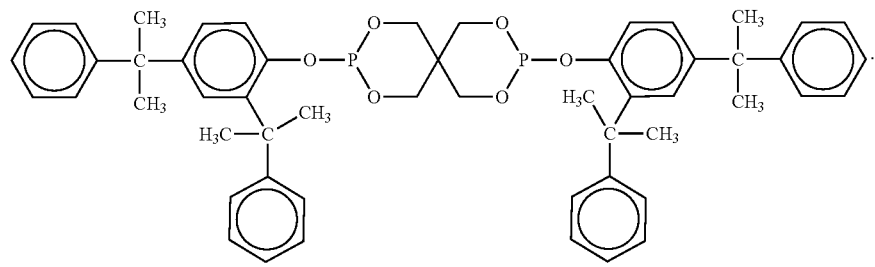

10. The process of claim 1 wherein
a mole ratio of said $PCl_3$ to said pentaerythritol is from about 1.9:1 to 2.2:1 inclusive;
said catalyst is added in an amount from about 1.0 to 15 weight percent based on said amount of pentaerythritol;
said phenol ranges from about 1 to 10 times a stoichiometric amount of said phenol; and
an initial reaction temperature for said reaction ranges from about 40° C. to 100° C. inclusive;
a subsequent reaction for said reaction after $PCl_3$ addition ranges from about 120° C. to 180° C. inclusive.

11. The process of claim 10 which further comprises a nitrogen sparge.

* * * * *